(12) United States Patent
Slocum

(10) Patent No.: US 6,464,705 B2
(45) Date of Patent: *Oct. 15, 2002

(54) JOINT SUPPORT

(75) Inventor: D. Barclay Slocum, Eugene, OR (US)

(73) Assignee: D. Barclay Slocum Trust Agreement, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,723

(22) Filed: Apr. 13, 2001

(65) Prior Publication Data

US 2001/0049525 A1 Dec. 6, 2001

Related U.S. Application Data

(63) Continuation of application No. 08/803,805, filed on Feb. 21, 1997, now Pat. No. 6,217,582.
(60) Provisional application No. 60/012,187, filed on Feb. 23, 1996.

(51) Int. Cl.[7] ............................................... A61B 17/64
(52) U.S. Cl. ........................................................ 606/55
(58) Field of Search .............................. 606/53, 54, 55, 606/57, 58, 59, 60, 61

(56) References Cited

U.S. PATENT DOCUMENTS

| 4,338,927 | A |   | 7/1982  | Volkov et al. |
| 4,483,334 | A |   | 11/1984 | Murray |
| 4,890,631 | A |   | 1/1990  | Hardy |
| 4,987,892 | A |   | 1/1991  | Krag et al. |
| 5,019,077 | A |   | 5/1991  | De Bastiani et al. |
| 5,160,335 | A |   | 11/1992 | Wagenknecht |
| 5,207,676 | A |   | 5/1993  | Canadell et al. |
| 5,376,091 | A |   | 12/1994 | Hotchkiss et al. |
| 5,468,241 | A |   | 11/1995 | Metz-Stavenhagen et al. |
| 5,545,166 | A |   | 8/1996  | Howland |
| 5,716,355 | A | * | 2/1998  | Jackson et al. ............... 606/61 |
| 5,797,908 | A |   | 8/1998  | Meyers et al. |

FOREIGN PATENT DOCUMENTS

WO        WO 90/02527   *  3/1990   ........... A61B/17/60

* cited by examiner

*Primary Examiner*—David O. Reip
(74) *Attorney, Agent, or Firm*—Kolisch Hartwell Dickinson McCormack & Heuser

(57) ABSTRACT

A joint support is attachable to a limb of an animal to limit movement of an associated limb joint substantially about a single axis. The joint support includes a radial element having a longitudinal axis and a transverse element having a longitudinal axis. The transverse element is pivotally connected to the radial element about an axis of rotation. The longitudinal axis of the radial element substantially intersects with the axis of rotation, and radial rotation of the radial element is restricted about the axis of rotation. The longitudinal axis of the transverse element is partially fixed relative to the radial element so that the same is substantially coplanar with the longitudinal axis of the radial element and substantially offset from the axis of rotation.

4 Claims, 2 Drawing Sheets

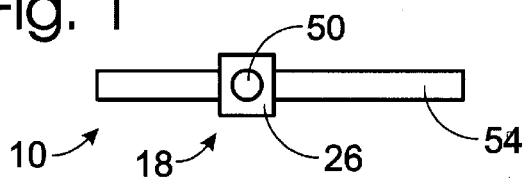
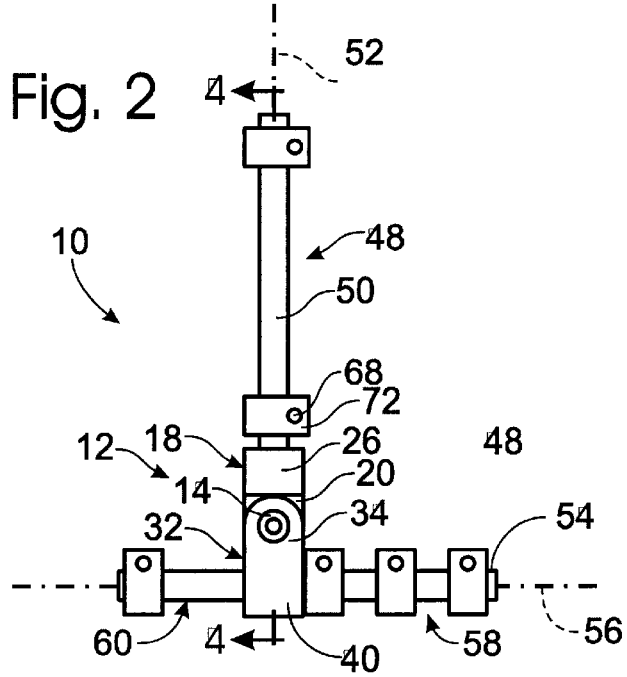
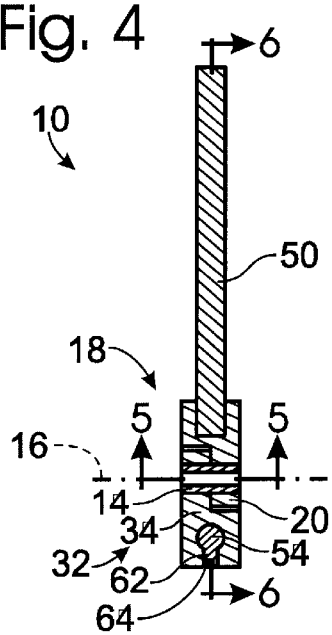
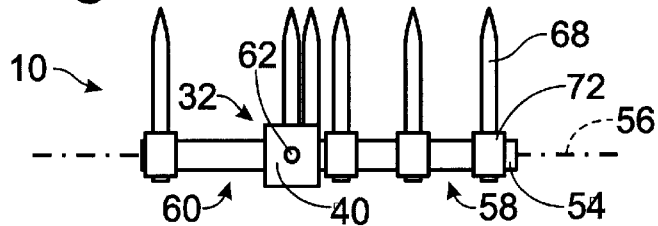
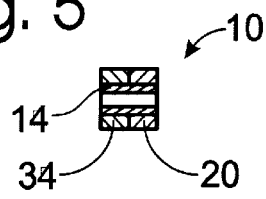
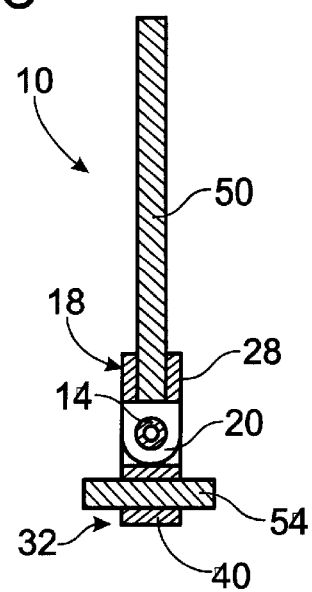

JOINT SUPPORT

CROSS-REFERENCE TO RELATED APPLICATIONS

This application is a continuation of U.S. patent application Ser. No. 08/803,805, filed Feb. 21, 1997, now U.S. Pat. No. 6,217,582, which claims priority from U.S. Provisional Patent Application Serial No. 60/012,187 filed on Feb. 23, 1996.

TECHNICAL FIELD

The invention relates generally to devices for supporting a joint in the limb of an animal, such as the joint between the tibia and the tarsus. The invention is attachable to desired bones of the animal via bone pins that penetrate the bone and extend through the animal flesh. Put another way, the joint support of the present invention is an external bone-joint fixator. The joint support has certain adjustable features, but once it is placed in an adjusted position, the joint support has a single degree of freedom about a hinge. When attached to pre-selected bones of an animal so that the hinge overlies a joint located between the bones, the joint support limits movement of that joint to the single degree of freedom of the support.

BACKGROUND ART

It is known to attach an external, mechanically hinged joint brace to a human limb, with the hinge overlying a joint in that limb. For example, U.S. Pat. No. 5,376,091 discloses several such braces. Another such conventional brace is known as the Richards-Illizarov System.

However, conventional joint braces have been constructed only for application to human joints. Such joint braces are ineffective for application to animals, at least in part because they are too complicated, and thus likely to be damaged or otherwise disturbed by the animal while wearing the brace. Conventional joint braces are also structurally inadequate for joints in animal limbs.

SUMMARY OF THE INVENTION

The present invention provides a joint support that effectively supports the joints of animals, and is particularly suited for use with domesticated animals such as dogs and cats. The invention generally includes a hinge, a radial support element attached to one side of the hinge, and a transverse support element attached to the other side of the hinge. The transverse element rotates relative to the radial element, with the transverse element rotating tangentially about the hinge. Tangential rotation means that the axial portion of the transverse element closest to the axis of rotation of the hinge defines substantially a circle as it rotates around the hinge, and the longitudinal axis of the transverse element is about tangent to the defined circle.

In the preferred embodiment, the hinge includes what is referred to as a radial block and a transverse block, with the radial block being that portion of the hinge that is attached to the radial support element, and the transverse block being that portion of the hinge that is attached to the transverse support element. The radial support element is fixed to the radial block, and the transverse support element extends through the transverse block to define an anterior portion and a posterior portion of the transverse element. In one embodiment of the present invention, the transverse element is releasably retained within the transverse block by a setscrew so that the proportion of the length of the anterior portion to the length of the posterior portion can be adjusted as necessary. Alternatively, the transverse element can be permanently affixed to the transverse block. In either embodiment, both the transverse and radial elements can be cut to any desired length.

BRIEF DESCRIPTION OF THE DRAWINGS

FIG. 1 is a top view of the present invention, showing the support elements and hinge, but exclusive of attached bone pins and clamps;

FIG. 2 is a side elevation of the joint support shown in FIG. 1, illustrating in schematic form the attached bone pins;

FIG. 3 is a bottom view of the joint support shown in FIG. 2;

FIG. 4 is a cross-sectional view of the joint support shown in FIG. 2, taken generally along line 4—4 in FIG. 2, and omitting attached bone pins;

FIG. 5 is a cross-sectional view of the joint support shown in FIG. 4, taken generally along line 5—5 in FIG. 4;

FIG. 6 is a cross-sectional of an alternative embodiment of the joint support shown in FIG. 4, taken generally along line 6—6 in FIG. 4, showing a alternate method of attaching the support elements to the hinge blocks, and shown with sections of the transverse support element removed.

Figure 7:
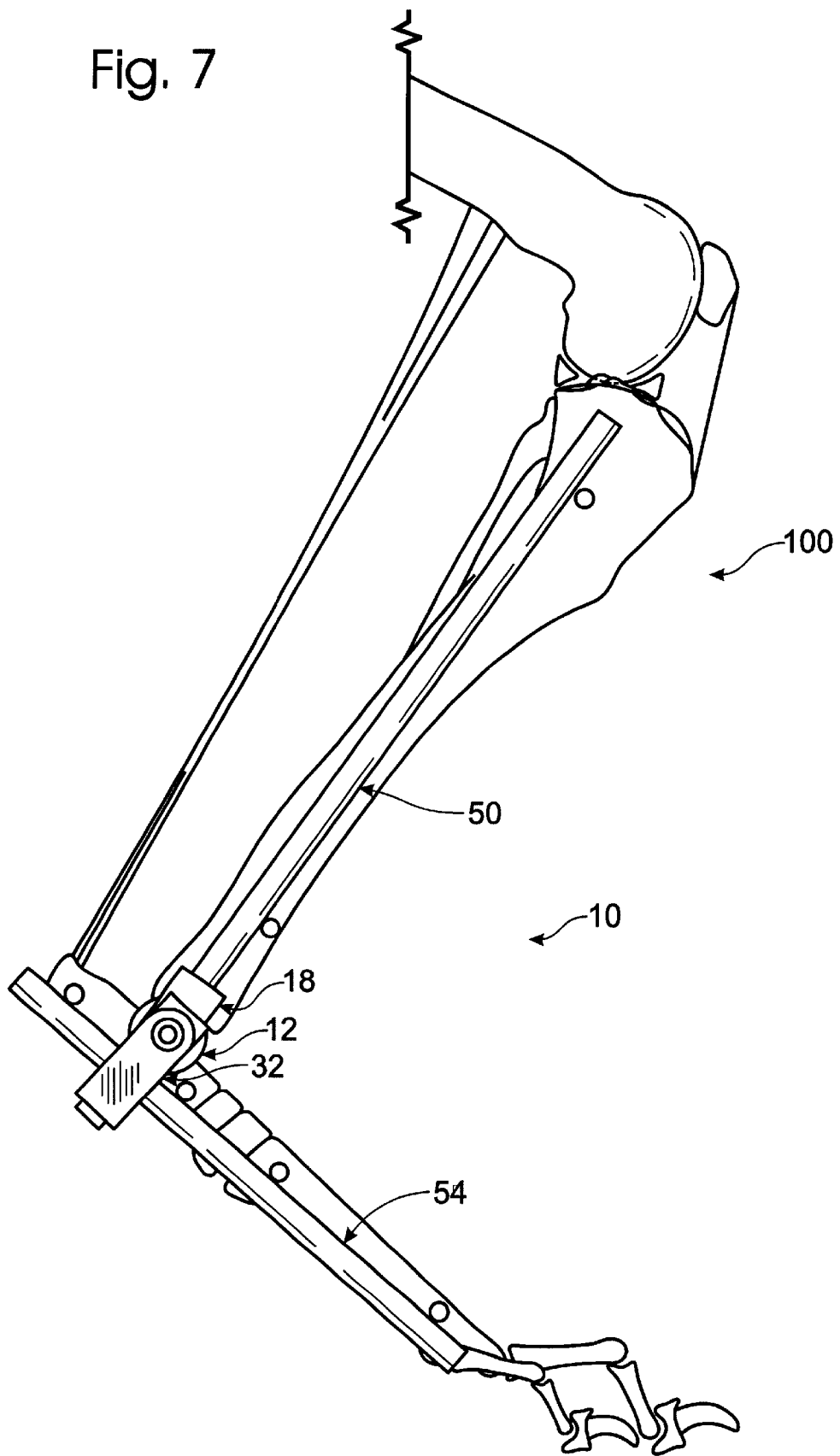
FIG. 7 is a medial view of a section of a dog skeleton, showing the tibia, tarsus and metatarsus attached to the joint support of the present invention.

DETAILED DESCRIPTION OF THE DRAWINGS AND BEST MODE FOR CARRYING OUT THE INVENTION

Referring generally to the drawings and focusing particularly on FIG. 2, a joint support according to the present invention is indicated generally at 10. Joint support 10 includes a hinge 12 defined by a pintle 14, preferably with a tubular passage 15 being formed in pintle 14 to define a longitudinal axis or hinge axis 16. Hinge 12 can be further defined to include a pair of hinge bodies.

One such hinge body is a radial block 18, having a tongue 20 in which is formed a pintle bore 22 defining a longitudinal axis 24. Radial block 18 further includes a body 26 in which is formed a radial bore 28 defining a longitudinal axis 30. Radial bore axis 30 is preferably substantially perpendicular to and intersecting pintle bore axis 24.

Another such block is a transverse block 32, having a tongue 34 in which is formed a pintle bore 36 defining a longitudinal axis 38. Transverse block 32 further includes a body 40 in which is formed a transverse bore 42 defining a longitudinal axis 44. Transverse bore axis 44 is preferably substantially perpendicular to and offset from pintle bore axis 38. A setscrew bore 46 extends through transverse block 32 to open into transverse bore 42, and is preferably substantially perpendicular to the transverse bore.

Joint support 10 includes support structure 48 operatively connected to hinge 12. One element of support structure 48 is a radial element 50 defining a longitudinal axis 52. Radial element 50 is connected to hinge 12 so that radial axis 52 is substantially perpendicular to and intersecting hinge axis 16. Another element of support structure 48 is a transverse element 54, defining a longitudinal axis 56, and in combination with radial element 50, defining a plane of support. Transverse element 54 includes an anterior portion 58 and a posterior portion 60, with anterior portion 58 being defined relative to posterior portion 60 by a line that extends perpendicularly from radial element 50 and intersects pintle bore axis 24. Longitudinal axis 56 is substantially perpendicular to and offset from hinge axis 16.

In the preferred embodiment, radial element 50 extends into radial bore 28, and transverse element 54 extends through transverse bore 42. Radial element 50 is fixed to hinge 12, preferably by threading radial element 50 into bore 28. The threaded engagement provides a relatively secure attachment, particularly when joint 10 is attached to an animal, yet also allows easy substitution of one length of radial element 50 for another.

Other methods of attaching radial element 50 to hinge 12 could be used, including pressing, gluing, brazing or welding radial element 50 into hinge 12. Alternatively, radial element 50 could be fixed relative to hinge 12 by a setscrew, not shown, or element 50 could be formed with an integral pintle bore, also not shown. Transverse element 54 is fixed relative to hinge 12 by a setscrew 62, having a tool socket 64 and defining a longitudinal axis 66. As with radial element 50, transverse element 54 could be threaded into transverse block 32, or formed with an integral pintle bore, not shown. Other means of pivotally interconnecting radial element 50 to transverse element 54, while preserving the relationship of elements 50 and 54 to the defined axis of pivoting are intended to be within the scope of the claims, set forth below.

For reference, bone pins are indicated generally at 68, each defining a longitudinal axis 70 that is usually substantially normal to the support plane defined by support structure 48. Joint support 10 can be used with other configurations of bone pins 68. Bone pins 68 are attached to support structure 48 as desired, with clamps 72 as shown in FIGS. 2–3.

FIG. 7 shows a representative example of joint support 10 being used to support the hock joint of a dog. Pertinent sections of a dog anatomy are shown generally at 100, including a tibia, a tarsus and a metatarsus.

INDUSTRIAL APPLICABILITY

The joint support of the present invention is applicable in any situation where it is desired to support a movable joint of an animal. It is particularly applicable to the support of the tibia-tarsal joint (hock joint) and the humerus-ulna/radius joint (elbow joint) of a dog or a cat.

I claim:

1. A joint support for attachment to a limb of an animal, the joint support limiting the movement of a joint in that limb to be substantially around a single axis, the joint support comprising:

a hinge constructed for use on the limb of an animal, and having two connected hinge blocks that pivot around a predefined hinge axis;

a radial element having a longitudinal axis, the radial element attached to one of the hinge blocks so that the longitudinal axis of the radial element is substantially perpendicular to the hinge axis, and so that the longitudinal axis of the radial element substantially intersects with the hinge axis, wherein the radial element is restricted to radial rotation around the hinge axis; and a transverse element having a longitudinal axis, the transverse element operatively connected to another of the hinge blocks so that the longitudinal axis of the transverse element is substantially offset from the hinge axis.

2. The joint support according to claim 1, wherein the longitudinal axis of the transverse element is substantially perpendicular to the axis of rotation so that the transverse element is restricted to about tangential rotation around the hinge axis.

3. A joint support for supporting the tarsus and metatarsus of an animal relative to the tibia, the joint support comprising:

a pintle having a longitudinal axis and constructed for use on the limb of an animal;

a radial block also constructed for use on the limb of an animal, and having formed therein a pintle bore, the pintle bore including a longitudinal axis, wherein the radial block is mounted on the pintle;

a transverse block also constructed for use on the limb of an animal, and having formed therein a pintle bore, the pintle bore having a longitudinal axis, wherein the transverse block is mounted on the pintle;

a radial element also constructed for use on the limb of an animal, and having a longitudinal axis, the radial element operatively connected to the radial block so that the longitudinal axis of the radial element is substantially perpendicular to the longitudinal axis of the pintle, and so that the longitudinal axis of the radial element substantially intersects the longitudinal axis of the pintle; and a transverse element also constructed for use on the limb of an animal, and having a longitudinal axis, the transverse element operatively connected to and extending through the transverse block to define an anterior portion and a posterior portion of the transverse element, with the longitudinal axis of the transverse element being substantially offset from the longitudinal axis of the pintle and substantially coplanar with the longitudinal axis of the radial element;

wherein, in use, the radial element is affixed to the tibia and the transverse element is affixed to the tarsus and metatarsus, with the posterior portion of the transverse element being generally affixed to the tarsus and the anterior portion of the transverse element being generally affixed to the metatarsus.

4. The joint support according to claim 3, wherein the longitudinal axis of the transverse element is substantially perpendicular to the axis of rotation so that the transverse element is restricted to about tangential rotation around the longitudinal axis of the pintle.

* * * * *